United States Patent [19]
Ferrari

[11] Patent Number: 6,107,102
[45] Date of Patent: *Aug. 22, 2000

[54] THERAPEUTIC MICRODEVICES AND METHODS OF MAKING AND USING SAME

[75] Inventor: Mauro Ferrari, Lafayette, Calif.

[73] Assignee: Regents of the University of California, Oakland, Calif.

[*] Notice: This patent issued on a continued prosecution application filed under 37 CFR 1.53(d), and is subject to the twenty year patent term provisions of 35 U.S.C. 154(a)(2).

[21] Appl. No.: 08/908,334

[22] Filed: Aug. 7, 1997

Related U.S. Application Data

[63] Continuation-in-part of application No. PCT/US96/09614, Jun. 7, 1996, and a continuation-in-part of application No. 08/481,760, Jun. 7, 1995, abandoned, and a continuation-in-part of application No. 08/485,818, Jun. 7, 1995, abandoned.

[51] Int. Cl.$^7$ ........................ A61K 49/00; A61B 49/00; A61B 5/055; A01N 25/26

[52] U.S. Cl. ...................... 436/518; 424/9.1; 424/9.2; 424/9.3; 424/932; 424/9.321; 424/9.322; 424/9.34; 424/9.341; 424/417; 424/422; 424/426; 424/450; 424/811; 424/812; 427/2.14; 427/213.3; 435/182; 436/64; 436/73; 436/518; 436/525

[58] Field of Search ............................ 424/9.1, 9.2, 9.3, 424/9.32, 9.321, 9.322, 9.34, 9.341, 417, 422, 426, 450, 181.1, 811, 812; 427/2.14, 213.3; 435/182; 436/518, 525, 64, 73, 829; 604/891.1, 48, 57

[56] References Cited

U.S. PATENT DOCUMENTS

| | | |
|---|---|---|
| 2,546,759 | 3/1951 | Lee et al. . |
| 3,970,518 | 7/1976 | Giaever . |
| 4,018,886 | 4/1977 | Giaever . |
| 4,241,176 | 12/1980 | Avrameas et al. . |
| 4,292,392 | 9/1981 | Ikeda et al. . |
| 4,419,340 | 12/1983 | Yolles . |
| 4,460,560 | 7/1984 | Tokes et al. . |
| 4,601,893 | 7/1986 | Cardinal . |
| 4,619,913 | 10/1986 | Luck et al. . |
| 4,698,238 | 10/1987 | Hayasaka et al. . |
| 4,793,825 | 12/1988 | Benjamin et al. . |
| 4,820,524 | 4/1989 | Berta . |
| 4,827,945 | 5/1989 | Groman et al. . |
| 4,828,563 | 5/1989 | Müller-Lierheim . |
| 4,898,732 | 2/1990 | Fernandez . |
| 4,902,288 | 2/1990 | Ingram . |
| 4,925,678 | 5/1990 | Ranney . |
| 4,951,675 | 8/1990 | Groman et al. . |
| 4,952,403 | 8/1990 | Vallee et al. . |
| 4,952,408 | 8/1990 | Rahman . |
| 5,069,216 | 12/1991 | Groman et al. . |
| 5,151,266 | 9/1992 | Morgan, Jr. et al. . |
| 5,182,111 | 1/1993 | Aebischer et al. . |
| 5,219,554 | 6/1993 | Groman et al. . |
| 5,378,475 | 1/1995 | Smith et al. . |
| 5,501,863 | 3/1996 | Rössling et al. . |
| 5,514,379 | 5/1996 | Weissleder et al. . |
| 5,527,528 | 6/1996 | Allen et al. . |
| 5,543,390 | 8/1996 | Yatvin et al. . |
| 5,635,383 | 6/1997 | Wu et al. . |
| 5,651,900 | 7/1997 | Kellet et al. . |
| 5,661,025 | 8/1997 | Szoka et al. . |
| 5,718,915 | 2/1998 | Virtanen et al. . |
| 5,770,076 | 6/1998 | Chu et al. . |

OTHER PUBLICATIONS

Cortesi et al., International Journal of Pharmaceutics 105:181–186, 1994.
Rahman, A., Journal of Liposome Research, 4(1):575–604, 1994.
Truong et al., Drug Delivery, 2:166–174, 1995.

*Primary Examiner*—James C. Housel
*Assistant Examiner*—Jana A. Hines
*Attorney, Agent, or Firm*—Peter J. Dehlinger; Michael L. Gencarella; Iota Pi Law Group

[57] ABSTRACT

A suspension of microfabricated microdevices for use in therapeutic applications is disclosed. The microdevices have a selected shape, and uniform dimensions preferably in the 100 nm to 10 Am range. Also disclosed are microfabrication methods for making such microdevices.

7 Claims, 12 Drawing Sheets

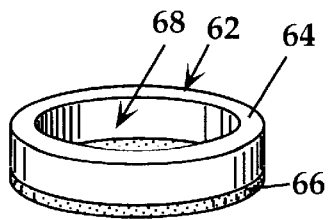 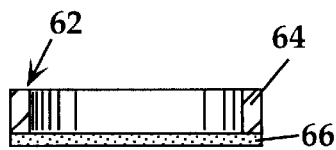 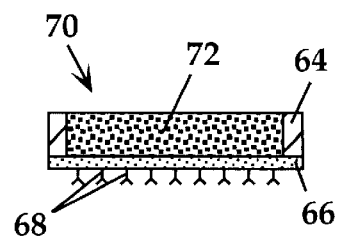
Fig. 5A  Fig. 5B  Fig. 5C
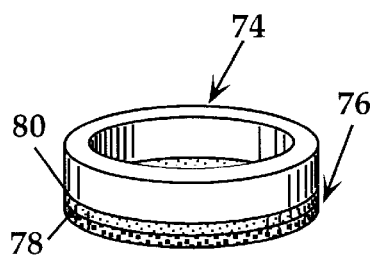 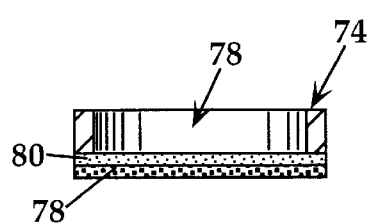 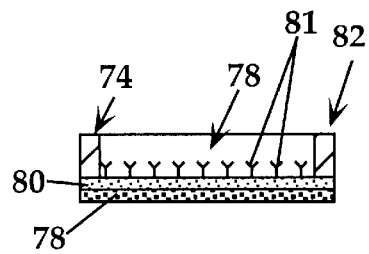
Fig. 6A  Fig. 6B  Fig. 6C
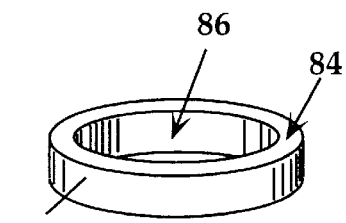 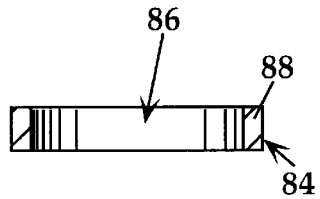 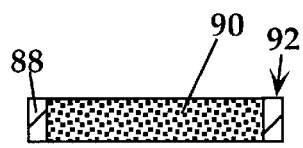
Fig. 7A  Fig. 7B  Fig. 7C
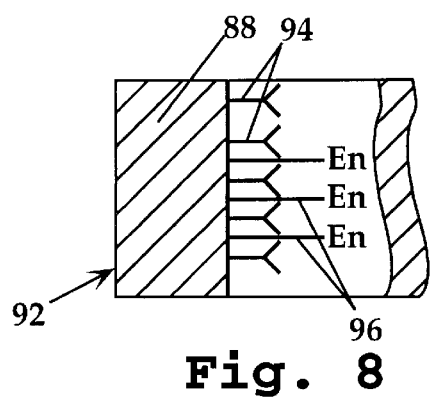
Fig. 8

THERAPEUTIC MICRODEVICES AND METHODS OF MAKING AND USING SAME

This application is a continuation-in-part of PCT Patent Application No. PCT/US96/09614, filed Jun. 7, 1996, herein incorporated by reference, and a continuation-in-part of U.S. patent application Ser. No. 08/481,760, filed Jun. 7, 1995 now abandoned, incorporated herein by reference. This application is also a continuation-in-part of U.S. patent application Ser. No. 08/485,818, filed Jun. 7, 1995 now abandoned, incorporated herein by reference.

FIELD OF THE INVENTION

The present invention relates to microstructural devices, and more particularly to microstructural devices for use in drug delivery to a body site.

BACKGROUND OF THE INVENTION

A variety of self-assembling particles have been used or proposed for drug delivery to a target site in a body. Lipid micellar particles formed of a surfactant provide certain advantages in solubilizing and delivering hydrophobic drugs, e.g., for intravenous drug delivery.

Liposome delivery systems have been employed for delivery of drugs to tissues and organs, e.g., liver and spleen, rich in macrophages of the reticuloendothelial (RES), for depot drug release in the bloodstream, and for site specific accumulation and drug release in solid tumors and sites of infection.

Liposomes offer a number of advantages over simpler micellar particles. The lipid bilayer shell in a liposome provides an internal aqueous compartment that is essentially isolated from bulk phase aqueous medium, allowing hydrophilic drugs to be sequestered at high concentration within liposomes, and further permitting loading of ionizable drugs by use of ion gradients across the liposomal membrane. Liposomes can also be processed to have selected sizes in the 30–200 nm size range for intravenous drug delivery. Finally, the outer liposome surfaces may be coated with a hydrophilic polymer, such as polyethylene glycol, to extend blood circulation time of the particles, and/or may be designed to carry surface-bound antiligand molecules for selective binding to target cells containing cell-specific surface ligands.

The use of synthetic polymers in drug delivery devices has focused on "smart polymers" a term given to polymers that form gels that have the ability to expand or contract in response to a specific stimulus, such as light, temperature or pH. Typically, such polymers will precipitate in solution or collapse with concomitant expulsion of gel pore contents. Synthetic polymers may be based on a number of types of monomeric units, including vinyl monomers, N-alkyl substituted acrylamides and the like. Copolymers have also been utilized in an attempt to combine or modulate the stimulus responsive properties of one or more known smart polymers. Polymer particles formed of negatively charged polymers have been designed for (i) rapid condensation (for drug entrapment) and decondensation (for drug release) or controlled-rate swelling and drug release, and (ii) high drug entrapment by an ion exchange mechanism.

The concepts of smart polymer particles and lipid-bilayer vesicles have been combined in drug-delivery particles of the type having a condensed-phase polymer core encased in a lipid-bilayer membrane, giving advantages of both types of drug-delivery systems. In particular, the polymer core of the particle can be loaded to high drug concentration, for rapid release by particle decondensation, and the lipid coating on the particles can be designed for targeting and/or for a target-specific triggering event which in turn leads to rapid particle decondensation.

It is evident that it is possible to design self-assembling lipid and/or polymer particles having various drug loading, targeting and triggering capabilities. Nonetheless, self-assembling particles of this type present two significant limitations. First, since the particles are typically spherical, the physical-contact area between the particles and target-site cells, for example, for particle binding to the cell, is more limited than would be the case with a particle having more planar surfaces. Secondly, and more importantly, the functioning of self-assembling particles, in terms of targeting and drug release, are limited in terms of (i) the particle materials (and therefore material properties) that can be employed, (ii) the types of drug storage and drug release mechanisms that can be realized, (iii) the number of targeting and therapeutic functions that can be built into the particles, (iv) the ability to place different functions at discrete locations on the particles, and (v) ability to be detected inside the body.

It is the purpose of the present invention to provide microdevices that significantly expand the shape, materials, and functions versatility and capabilities over self-assembling drug-delivery particles.

SUMMARY OF THE INVENTION

The invention includes, in one aspect, a microstructural device for use in administering a therapeutic agent to a selected target site in a subject. The microdevice has a selected non-spherical shape and uniform dimensions (e.g., a disk shape), and contains the therapeutic agent in a form where the activity of the therapeutic agent is expressed by exposure of the microdevice to the biochemical environment of the target site after administration to the subject.

In a related aspect, the invention includes a suspension of microdevices for use in administering a therapeutic agent to a selected target site in a subject. The microdevices have a selected non-spherical shape and uniform dimensions and contain the therapeutic agent in a form in which the activity of the therapeutic agent is expressed by exposure of the microdevice to the biochemical environment of the target site after administration to the subject. The microdevices may have surface-bound, marker-binding molecules effective to bind to a marker carried on the surface of cells at such target site.

Where the suspension is used for targeting selected cells or tissue via the bloodstream, the microdevices may be coated with a hydrophilic polymer, such as polyethylene glycol or glycocalyx polymer, effective to enhance maintenance of the microdevices in suspension. The hydrophilic polymer may be conjugated to vesicle-forming lipids, where the microdevices are coated with a lipid film containing such vesicle-forming lipids. The microdevices may contain a marker-binding molecule bound to the free ends of at least a portion of the polymer, this molecule being effective to bind to a marker carried on the surface of such target cells or tissue.

Where the suspension is used in parenteral administration to a subject, the microdevices may have a selected maximum dimension in the range between 0.1 and 3 microns. For solid-tumor targeting such microdevices preferably have a maximum dimension less than about 150 nm.

Where the suspension is used in delivering a therapeutic compound to the interstitial space of a target region characterized by a target-specific marker on the basement membrane forming the vasculature of the target region, the microdevices may contain surface-bound marker-binding molecule effective to bind to such marker, and an enzyme effective to lyse the basement membrane. One preferred enzyme is a type IV collagenase. The enzyme may be covalently attached to a surface region of the microdevices, or may be contained in the microdevices in releasable form, e.g., upon erosion of the microdevices. For example, the enzyme may be enclosed in a compartment which is sealed by, e.g., a biodegradable layer, for release upon biodegradation of the layer at the target site.

In one general embodiment, the microdevices are formed of a material designed to erode in body fluid at a selected bioerosion rate. As examples, the microdevices may be formed of iron, titanium, gold, silver, platinum, copper, and alloys and oxides thereof. Alternatively the microdevices may be formed of a biodegradable polymer material.

In one embodiment, the microdevices are composed of a condensed-phase polymer material effective to decondense, at a selected rate, when exposed to plasma.

In another embodiment, the microdevices are substantially disc-shaped, and have a laminated structure containing two or more layers, where adjacent layers are formed of different materials. As example, the microdevices may have a trilaminate structure composed of an interior layer, formed said therapeutic-agent microstructure, sandwiched between a pair of exterior coating layers, at least one of which forms said substrate, where the coating layers have a slower rate of bioerosion than the interior layer, and the therapeutic compound is embedded in said intermediate layer, for release as the intermediate layer is eroded.

In still another general embodiment, the microdevices have shielded wall surfaces that are substantially inaccessible to biological cells. These wall surface may be coated with therapeutic agents, such as therapeutic antibodies or the like. Exemplary microdevices of this type include ring shaped and cup-shaped devices.

For use in directing the microdevices to a target site by a magnetic field, or retrieving the devices from a site by a magnetic field, the microdevices contain a magnetic material.

For use in radiotherapy, or monitoring of the localization of the devices at a selected target site, the microdevices contain a radioactive material.

For use in boron neutron capture therapy (BNCT), the microdevices contain boron.

Also disclosed is a microfabrication method for producing microdevices of the type described. The method includes exposing a sheet of microdevice material to a photoablating light source through a photomask, to form a reticular lattice pattern on the sheet corresponding to the desired microdevice size and shape. The photoablating is continued until the desired degree of ablation is achieved.

These and other objects and features of the invention will become more fully apparent when the following detailed description is read in conjunction with the accompanying drawings.

BRIEF DESCRIPTION OF THE DRAWINGS

FIGS. 1A–C, 2A–C, 3A–C, 4A–C, 5A–C, 6A–C, and 7A–C, illustrate various embodiments of microstructures and microdevices constructed in accordance with the invention, shown in perspective views (FIGS. 1A–7A), and cross-sectional views (remaining figures);

FIG. 8 is an enlarged section of the disk-shaped microstructure in FIG. 7C, showing surface bound antibody and therapeutic agents on the inner wall surface thereof;

DETAILED DESCRIPTION OF THE INVENTION

I. Definitions

Unless indicated otherwise, the terms below have the following meaning.

"Microstructures" or "microparticles" or "microfabricated structures" or "microfabricated particles" are particles formed by microfabrication methods.

"Microdevices" or "microfabricated devices" are microstructures that have been additionally prepared to include biological agents as coatings and/or therapeutic agents.

"Microfabrication methods" refer to methods employing photomasking or patterned beam irradiation of a substrate to produce desired surface pattern features in the substrate. Exemplary microfabrication methods include photolithography, x-ray lithography and electron-beam lithography.

The "biochemical environment of the target site" refers to one or more intrinsic physiological conditions at the target site, such as pH, salt conditions, temperature, or the presence of target-specific cell surface markers or enzymes, effective to initiate and promote release of a therapeutic agent from the microdevices of the invention. The target site may be a specific cell, tissue or organ type, the interstitium of a tissue or organ, a vascular site, or blood or plasma.

"Bioerodable" refers to a material that is dissolvable in physiological medium (e.g., an erodible metal), or a biocompatible polymeric material that can be degraded under physiological conditions by physiological enzymes and/or chemical conditions, e.g., in a reducing or reduced-pH environment.

II. Microdevices

The present invention provides microdevices that are useful therapeutically in a variety of in vitro, in vivo and ex vivo applications, in particular, intravascular applications. The microdevices have a selected non-spherical shape, uniform dimensions and contain a therapeutic agent in a form where the activity of the agent is expressed by exposure of the microdevice to the biochemical environment of a selected target site.

A. Representative Embodiments

The shape, size and composition of a microdevice of the present invention depend on the selected application. For example, devices designed to be used in typical intravascular applications are preferably substantially disk-shaped, cup-shaped, or ring-shaped. Exemplary embodiments of such disk-, cup- or ring-shaped devices are illustrated in FIGS. 1–7, in top perspective views (FIGS. 1A–7A) and cross-sectional views (FIGS. 1B–7B and 1C–7C).

Figure 1A:
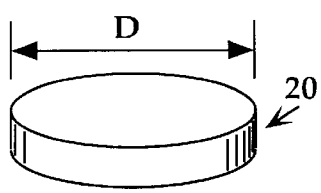
Figure 1B:
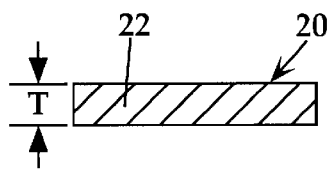
Figure 1C:
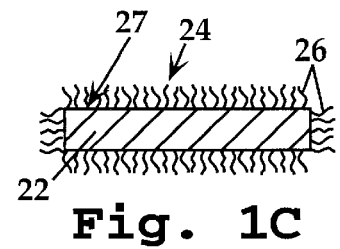

FIGS. 1A and 1B show a disk-shaped microstructure 20 composed of a thin disk with diameter D between about 50 nm to about 3 microns and a thickness between about 10 nm and about 1 micron. The disk is formed of a single material 22 which may contain the therapeutic agent (e.g., a drug in a polymer matrix). Although non-erodible materials may be used, particularly for ex vivo applications, the preferred devices are formed of bioerodable materials, as described below.

The device may further be coated partially or completely with a coating 24 of hydrophilic polymer chains, such as chains 26, to form a coated microdevice 27. Typically these chains are added after formation of the microstructures groups. Preferred hydrophilic chains are polyethylene glycol (PEG) chains and synthetic glycocalyx, which are intended to either enhance the solubility of the device or, in the case of PEG, to extend blood circulation of the device. Methods of derivatizing a variety of metal surface with polymer chains are well known. For example, chains containing thiol end groups at one chain end can be reacted with a metal surface under conditions effective to form thioether linkages. Similarly, where the disk material is a polymer, a variety of surface attachment chemistries, e.g., involving carboxyl groups in the disk material and amine or hydroxyl groups in the polymer chains, are available for covalent linkage to the disk material. Other approaches to attaching hydrophilic polymer chains to microstructures are described below.

Figure 2A:
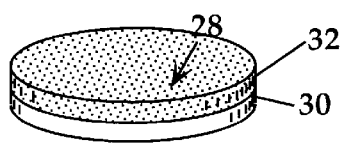
Figure 2B:
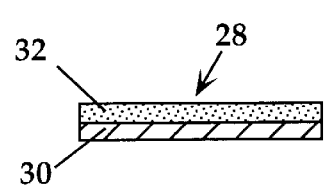
Figure 2C:
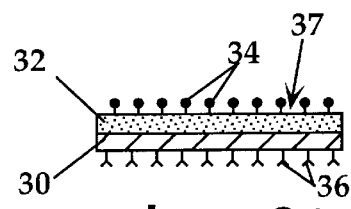

Microstructures of the present invention may be formed of two or more layers of different materials. For example, FIGS. 2A and 2B show a microstructure 28 formed of two layers 30, 32. As indicated in FIG. 2C, the structure may have different biological coatings on the two different-material surfaces, forming a coated microdevice. For example, the upper surface of the device may be coated with molecules, such as molecules 34, of a therapeutic agent, and the lower surface, with molecules, such as molecules 36, of an antibody, forming a microdevice 37. The antibodies illustrated are intended for targeting the microdevices to selected target sites, e.g., selected blood, tissue or organ cells. Methods for attaching antibody or other polymer binding agents to an inorganic or polymeric support are detailed, for example, in Taylor, R., Ed., *PROTEIN IMMOBILIZATION FUNDAMENTALS AND APPLICATIONS*, pp. 109–110 (1991).

Figure 3A:
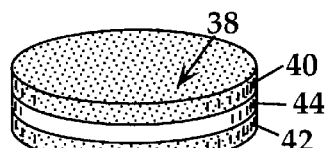
Figure 3B:
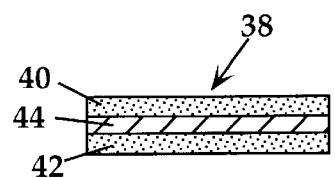
Figure 3C:
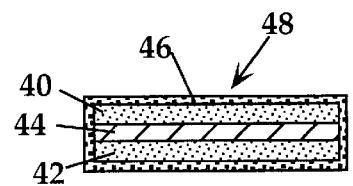

FIGS. 3A and 3B show a disk-shaped trilaminate microstructure 38 having outer layers 40, 42, and an center layer 44. In the embodiment shown, the outer layers are composed of one material, while the center layer consists of a different material, for example, a material that gives faster bioerosion than the outer layers. Other embodiments may contain additional layers. As indicated in FIG. 3C, the microstructure may be coated with a film 46, such as a corrosion delay film, forming a microdevice 48. The corrosion delay layer is typically made of a material that gradually dissolves in the biochemical environment of the target. Examples of such coatings include titanium, gold, silver, platinum, copper, and alloys and oxides thereof.

The thickness of the corrosion delay layer may be selected to, for example, provide the desired lifetime of the device in the bloodstream, or to allow the device to bind to its target before therapeutic agent is released. These layers may be applied by standard metal deposition procedures.

It will be appreciated that the surface coatings and films in the microdevices can have any of a number of different function. For example they can serve as structural elements of the device itself, e.g., an anticorrosive coating; as the therapeutic moiety, e.g., in the case of antibodies directed against a foreign antigen, as the targeting moiety (e.g., tumor-specific antibodies); as an element which confers other selected properties on the microdevice, e.g., glycocalyx coating; or a therapeutic agent designed to erode over time. It will be recognized that various permutations of laminate structures and coatings, such as those illustrated in FIGS. 1–3, are contemplated.

Figure 4A:
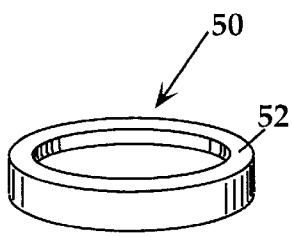
Figure 4B:
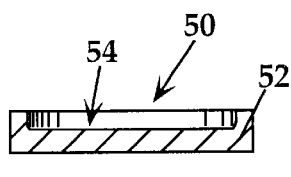
Figure 4C:
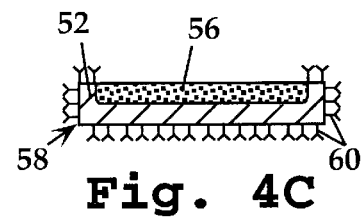

FIGS. 4A and 4B show a microstructure 50 constructed according to another general embodiment of the invention. This structure includes a generally cup-shaped body 52 having a cavity 54. Referring to FIG. 4C, the cavity can be filled with one or more materials, such as material 56, which form the "core" of the microdevice, and may contain, for example, the therapeutic agent, forming a microdevice 58. The device may also contain coating(s) different from coating(s) on other parts of the device, such as the coating of antibodies, such as antibodies 60, for targeting the device to a selected body site.

FIGS. 5A and 5B show a similar type of cup-shaped microstructure 62, but here composed of a ring-shaped wall member 64 formed of one material and a planar bottom member 66, forming an internal cavity 68. This construction may facilitate, for example, the attachment of different moieties to the top and bottom portions of the device, as indicated by attachment of target-specific antibodies, such as at 68, to form a microdevice 70 shown in FIG. 5C. The cavity in the microdevice is filled with a selected material 72, as above.

A similar type of cup-shaped microstructure is shown at 74 in FIGS. 6A and 6B. In this microstructure, the bottom portion is formed of a laminate 76 composed of two different-material layers 78, 80. For example, layer 80 may be formed of a relative low-density erodible polymer, to impart an overall density to the particle close to that of an aqueous suspension medium, to achieve a more stable suspension of microparticles for therapeutic applications. The other layer may be, for example, an easily erodible material and/or contain an entrapped therapeutic compound, and/or be formed of a ferromagnetic material.

As shown in FIG. 6C, the internal cavity of the structure, indicated at 78, may be constructed to contain a wall coating of biological molecules, such as antibodies 81, to form a microdevice 82. According to an important feature of the invention, and as well be described below, the antibodies are effectively shielded sequestered from a body's immune-response system, thus permitting the antibodies to carry out desired binding functions, e.g., removal of toxins, viral particles, cholesterol-containing particles, without the antibodies themselves provoking an immune response in the host organism.

FIGS. 7A and 7B illustrate a ring-shaped microstructure 84 having an internal core 86 defined by an annular structural member 88. The core can contain, for example, a coating of a therapeutic agent or mixture of agents, as indicated at 90, forming a microdevice 92. An exemplary coating is shown in enlarged view in FIG. 8, and includes a combination of antibodies, such as antibody molecules 94, and enzymes, such as enzyme molecules 96. In a particular embodiment, the antibodies are directed against a lipoprotein particle, e.g., Lp(a), and the enzyme is an esterase or protease enzyme capable of at least partially degrading the particles, once bound within the core of the microdevice.

The optimal dimensions of microdevices of the present invention similarly depend on the application. The maximum dimension of the devices (the diameter of the disk in the case of disk-shaped devices) is typically in the range between 0.05 and 5 microns. For example, in applications where the device is designed to extravasate through pores lining the walls of capillaries supplying a tumor, the maximum dimension of the device is preferably less than about 150 nm, to allow passive movement of the device through the vasculature. In applications where the devices are designed to circulate or to bind to a target without extravasation, they may be larger. It is recognized, however, that particles larger than 200–400 nm may be rapidly cleared from the bloodstream and in addition, cannot be sterilized by filter sterilization.

The minimum dimensions of the microdevices are constrained only by the microfabrication process itself. As is described more fully below, it is recognized that "traditional" photolithography is limited to the microfabrication of structures greater than about 0.5 microns, but that substantially smaller structures (with dimensions contemplated in the present invention—e.g., 50–200 nm diameter devices) may be produced using known X-ray and/or electron beam lithography methods.

Certain layers and coating which may be contained in a device such as described above (e.g., a layer of targeting antibodies) can be as thin as a single layer of molecules. The minimum size again depends on the application. For example, in the case of devices made from biodegradable materials, the smaller the device, the faster it will dissolve. The stability of device of the present invention in a particular application may be readily determined by one of skill in the art using tagged (e.g., fluorescent or radiolabelled) devices in a model system.

Another important property of microstructures and microdevices is the bioerodability of the material employed in making the microstructure. Some metals, such as iron, are rapidly dissolved in serum, whereas others, such as gold, are much more slowly eroded. Therefore, to achieve a desired rate of erosion, metals may be mixed in alloy.

A variety of bioerodable polymers, including polyglycolic, polylactic, polyurethane, celluloses, and derivatized celluloses may be selected, and a variety of charged polymers, such as heparin-like polysulfated or polycarboxylated polymers are suitable in forming one or more of the microstructure layers. The latter polymers have the advantage of being swellable and shrinkable under selected ionic conditions, and can be loaded to high drug concentration by ion-exchange effects, for drug release under physiological conditions. Such polymers are described in PCT application WO/US94/01924 for "Condensed-Phase Microparticle Composition and Method" which is incorporated by herein by reference.

Any of the above-described microstructure materials may be selected to enhance the detectability of the microdevices, e.g., as diagnostic microdevices or for purposes of tracking the biodistribution of therapeutic microdevices. For example, the microdevice may be fabricated with X-ray or MRI-resolvable material. X-ray-resolvable materials include iron, silicon, gold and gadolinium. MRI-resolvable materials include gadolinium and iron.

Further, the microdevices can be tagged so as to allow detection or visualization. For example, microdevices are rendered radioactive by implantation or surface attachment of radioactive isotopes such as I-123, I-125, I-131, In-111 and Tc-99m. Radioactive devices concentrated at a site of disease can be identified by a radiation detector such as the γ-ray cameras currently used in scintigraphy (bone scans), resulting in identification and localization of such regions. Microdevices can also be tagged with fluorescent molecules or dyes, such that a concentration of microdevices can be detected visually.

The structural material used in forming the microstructure is selected to achieve desired erodability and drug release properties. In the case of drug release, the structural material may be one or more biodegradable polymers. Classes of biodegradable polymers include polyorthoesters, polyanhydrides, polyamides, polyalkylcyanoacrylates, polyphosphazenes, and polyesters. Exemplary biodegradable polymers are described, for example, in U.S. Pat. Nos. 4,933,185, 4,888,176, and 5,010,167. Specific examples of such biodegradable polymer materials include, for example, poly(lactic acid), polyglycolic acid, polycaprolactone, polyhydroxybutyrate, poly(N-palmitoyl-trans-4-hydroxy-L-proline ester) and poly(DTH carbonate).

As indicated above, the polymer matrix may also contain a hydrogel, such as a cross-linked polymer of hydroxyethyl methacrylate and ethylene dimethacrylate or a cellulose ether-type hydrogel (Doelker, in *HYDROGELS IN MEDICINE AND PHARMACY. VOL. II,* Peppas, Ed., CRC Press, Boca Rotan, Fla., pp. 115–154 (1987)). Hydrogels are typically water-swellable matrices containing dispersed or dissolved drug. Hydrogels are preferably used in combination with water-insoluble drugs, such as steroids (Zentner, et al., *J. Pharm. Sci.* 68:970 (1979)), and high molecular weight drugs such as insulin (Davis, *Experientia* 28:348 (1972)), enzymes (Torchilin, et al., *J. Biomed. Mater. Res.* 11:223 (1976)), and vaccine antigens (Bernfield, et al., *Science* 142:678 (1963)).

The solubility of an active agent in a particular polymer can be estimated by the use of solubility parameters (Hildebrandt, et al., *THE SOLUBILITIES OF NONELECTROLYTES,* Reinhold, N.Y. (1950)), where close solubility parameter values between an active agent and polymer tend to favor compatibility and solubility. The active agent will typically be dispersed or dissolved in the polymer matrix. Alternatively, the active agent may be covalently attached to the polymer backbone through reactive pendant chains that can be cleaved, typically by hydrolysis. In utilizing this approach, the device will also contain a means for providing controlled release of active agent from the polymer backbone, such as by cleavage of the covalent attachment.

The diffusion or release properties of the polymer matrix can be modified by various techniques, such as crosslinking, chemical structure modification, blending of two or more polymers, or by the addition of plasticizers (e.g., butylbenzylphthalate, trioctylphosphate, dioctylphthalate, glycerol, polyethylene glycol, and polypropylene glycol) or solvents. The matrix may also contain additional components, such as preservatives or bacteriostatic agents, e.g., methyl hydroxybenzoate, chlorocresol, benzalkonium chlorides, and the like.

Typically the therapeutic agent is attached to or incorporated into the polymer layer after microfabrication, to prevent exposure of the agent to the chemical etching procedures discussed in the section below.

B. Microfabrication of the Microstructures

The structural portion or layer (i.e., microstructure) of the microdevices of the present invention may be microfabricated using any suitable microfabrication method, such as the photolithography and photoablation methods detailed below. It will be appreciated that the microdevices can also be microfabricated using other microfabrication methods known to those skilled in the art, such as x-ray or electron beam lithography. Electron beam lithography has been used to produce sub-micron circuit paths (e.g., Ballantyne, et al., *J. Vac. Sci. Technol.* 10:1094 (1973)), and may be used (e.g., in combination with near field scanning microscopy) to generate and image patterns on the nanometer scale (see, e.g., INTRODUCTION TO MICROLITHOGRAPHY, Thompson, et al., Eds., ACS Symposium Series, Washington D.C. (1983)).

FIGS. 9A–9E illustrate the steps in forming a disk-shaped microstructure 100 (FIG. 9E) by photolithographic techniques. As shown, the structure includes two layers 102, 104, which will be formed of two identically numbered layers (102 and 104) forming a planar expanse 106. This laminate expanse is formed according to conventional methods for deposition of metal layers, e.g., chemical vapor deposition, sputtering or the like, and/or methods for producing thin polymer sheet material.

As a first step in the process, the laminate expanse is attached or otherwise bonded to a sacrificial layer 108, such as phosphorous doped silicon dioxide, deposited by chemical vapor deposition, and the top of the laminate is coated with a photoresist layer 110. Suitable negative- or positive-resist material are well known, e.g., INTRODUCTION TO MICROLITHOGRAPHY, Thompson, et al., Eds, ACS Symposium Series, Washington D.C (1983). Additional details on microfabrication methods useful in the manufacture of devices according to the present invention are described in, e.g., co-owned PCT patent publications WO 95/24261, WO 95/24472 and WO 95/24736.

The coated laminate is irradiated through a photomask 112 having a series of circular openings, such as opening 116, corresponding in size to the desired size of the microstructures. Methods for forming photomasks having desired photomask patterns are well known.

Figure 9A:
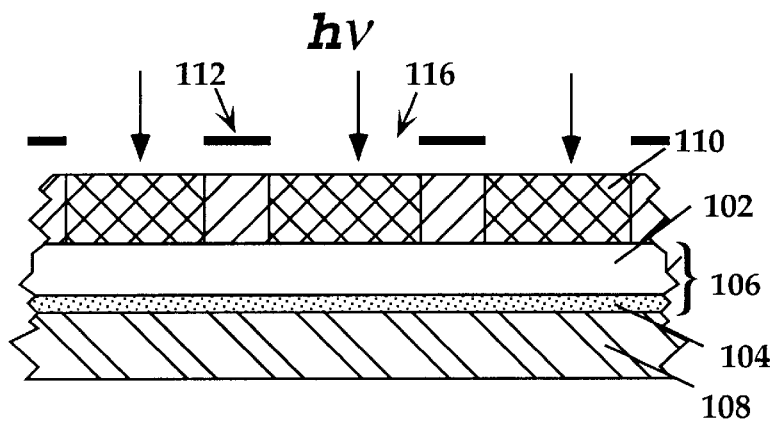
FIGS. 9A–9E illustrate steps in the photolithographic fabrication of microstructures of the type illustrated generally in FIG. 2A.
Figure 9B:
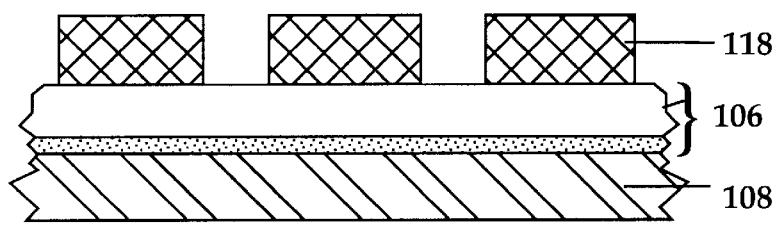
Figure 9C:
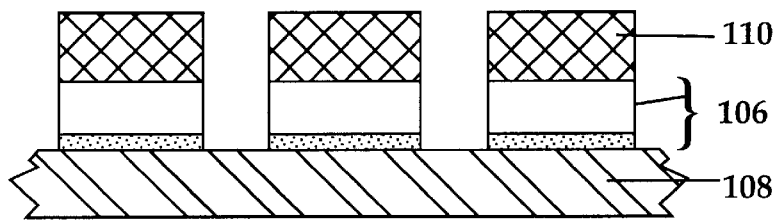

In the embodiment described with reference to FIGS. 9A–9E, the photoresist is a negative resist, meaning that exposure of the resist to a selected wavelength, e.g., UV, light produces a chemical change (indicated by cross hatching) that renders that altered resist resistant to etching by a suitable etchant. The appearance of the coated laminate after photomask irradiation UV and etching is shown in FIG. 9B. As seen, laminate 106 is now covered by a plurality of discrete disk-shaped resist elements, such as elements 118, corresponding in size to the planar dimensions of the desired microstructures.

The laminate is now treated with a second etchant material effective to dissolve the laminate in the exposed areas of the laminate. In the case of a laminate metal layer, the etchant may be a suitable acid solution; in the case of a laminate biodegradable polymer layer, the etchant could be an enzyme solution, an aqueous solution having a pH effective to break down the polymer, or an organic solvent known to dissolve the particular polymer. It will be appreciated that in the case of laminates, more than one etchant solution may be required. The laminate, after complete etching, has the appearance of FIG. 9C, which shows a series of disk-like, resist-coated elements on the sacrificial layer.

Figure 9D:
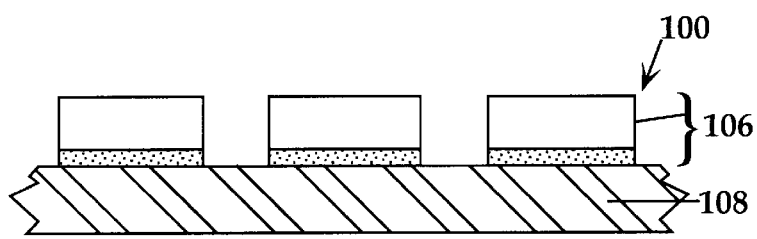
Figure 9E:
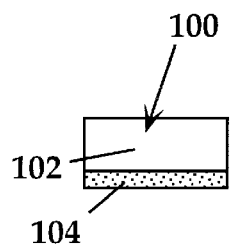

In the final preparation steps, the resist is removed by suitable chemical treatment (FIG. 9D), and then the sacrificial layer is removed, again by conventional chemical treatment, leaving the individual microstructures, such as microstructure 100 (FIGS. 9D, 9E).

Figure 10A:
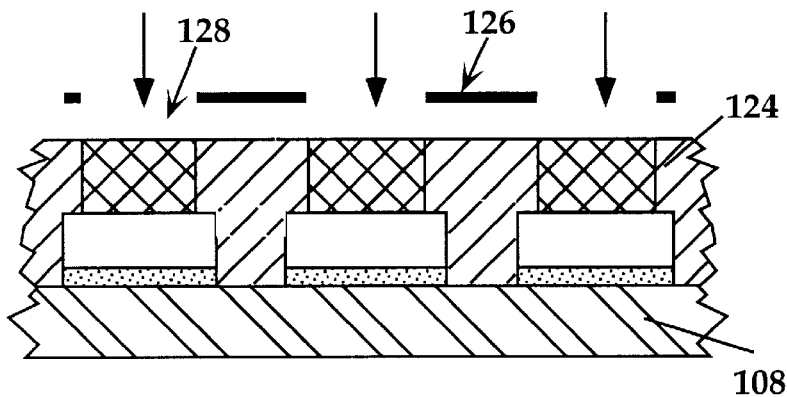
FIGS. 10A–10E illustrate steps in the photolithographic fabrication of microstructures of the type illustrated generally in FIG. 5A.
Figure 10B:
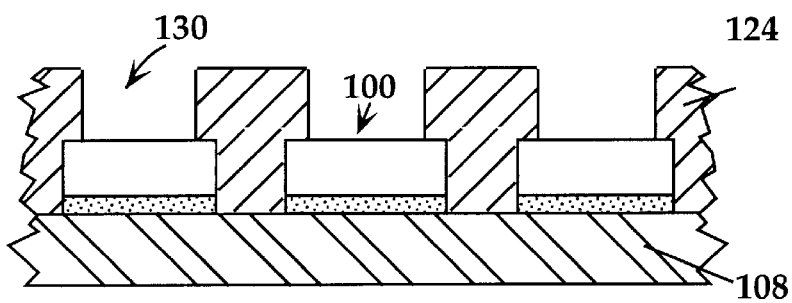
Figure 10C:
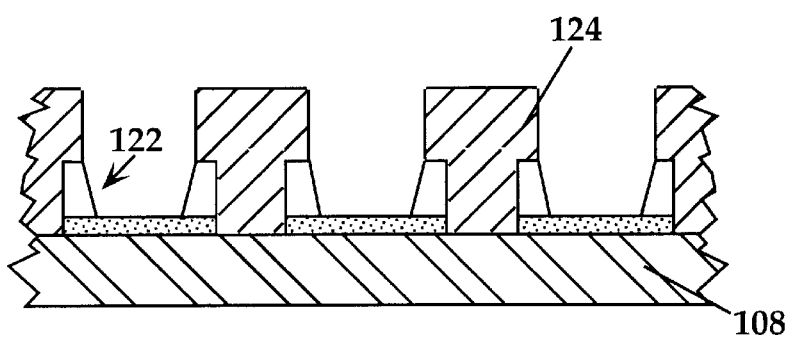
Figure 10D:
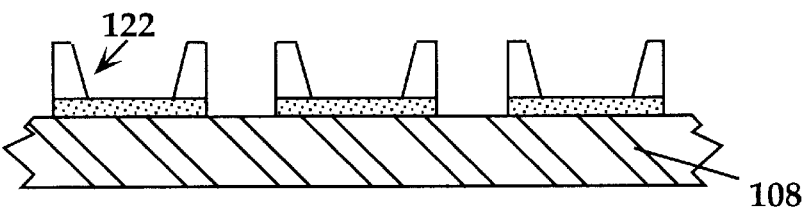
Figure 10E:

FIGS. 10A–10E illustrate further photolithographic processing effective to produce cup-shaped microstructures, such as shown at 122 in FIG. 10E. In this processing, the etched laminate/sacrificial layer structure or substrate shown in FIG. 9D is further coated with a positive resist material 124, as shown in FIG. 10A. The coated laminate is then irradiated through a photomask 126 having a series of circular openings, such as opening 128, whose diameters correspond to the desired "internal" diameters of the microdevices. The mask is aligned with the substrate, as shown, so that the mask openings are in registry with the already formed discs in the substrate.

Irradiation of the substrate through the photomask causes photo-induced changes in the resist (indicated by cross hatching) that render the irradiated regions susceptible to a selected etchant. The appearance of the coated laminate after photomask irradiation UV and etching is shown in FIG. 10B. As seen, this treatment has produced a cylindrical opening, such as opening 130, in the center of each microstructure 100 in the substrate.

The laminate is now treated with a second etchant material effective to dissolve the upper laminate layer in the exposed areas of the laminate, producing the series of microstructures 122 seen in FIG. 10C. Removal of the photoresist (FIG. 10D) and sacrificial layers produces the free microstructures 122 shown in FIG. 10E.

It will be appreciated that the microstructures formed as just described may be further treated by standard photolithographic techniques to produce other desired surface features and or layers. Further, indentations or cavities may be filled with a material different from the microstructure material by known methods. For example, such an indentation or cavity may be filled with a selected therapeutic protein, such as interferon, insulin, various proteases, luteinizing releasing hormone and its analogs, and the like.

The therapeutic substance may also be coated onto one or more surfaces of the microfabricated microstructure. For example, U.S. Pat. No. 5,200,051 describes photolithographic methods for depositing perm-selective and proteinaceous layers on a planar substrate. These same techniques can be applied to the present invention, to incorporate such layers in the microdevices of the invention.

In another general approach, the microdevices are patterned from a substrate by excimer laser photoablation techniques. Methods of laser micromachining or dry etching have been described, e.g., U.S. Pat. Nos. 5,368,430, 4,994, 639, 5,018,164, 4,478,677, 5,236,551, and 5,313,043. This method is most suited to a polymeric substrate, because of the ease with which a laser beam can photoablate polymer structures.

Figure 11A:
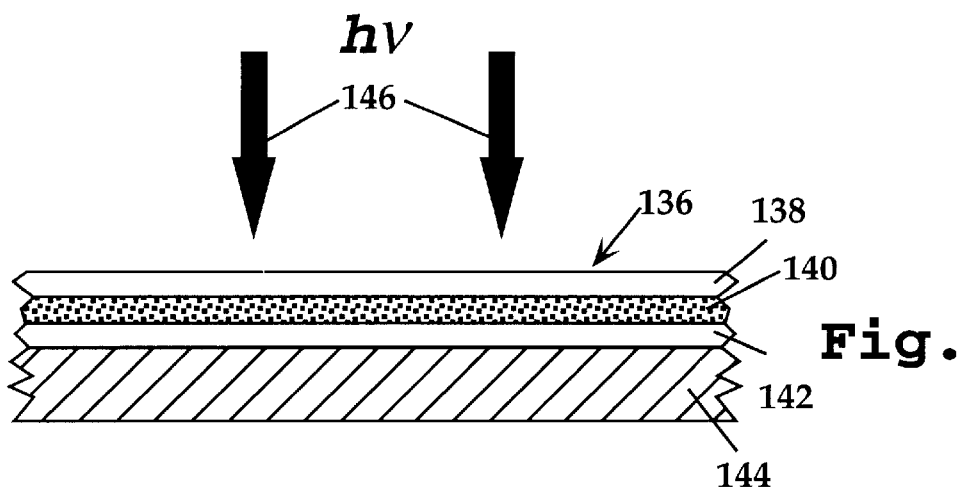
FIGS. 11A–11D illustrate steps in the fabrication by laser ablation of microstructures of the type illustrated generally in FIG. 3A.
Figure 11B:
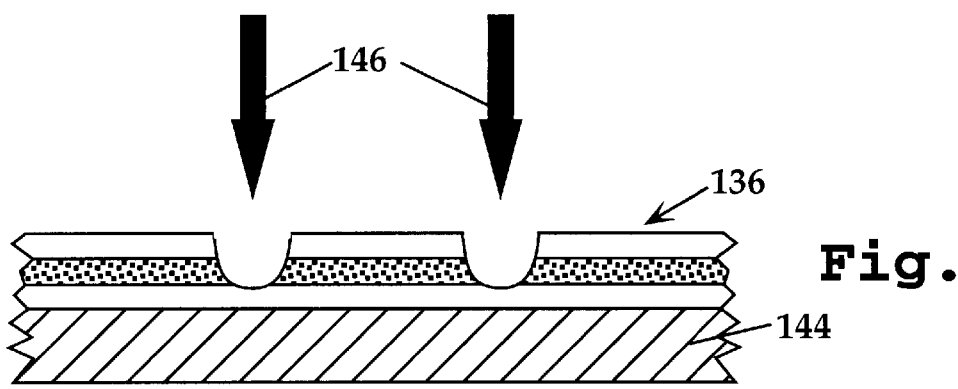
Figure 11C:
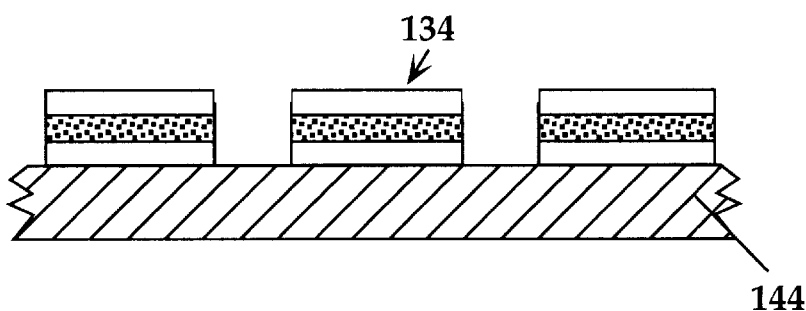
Figure 11D:

FIGS. 11A–11D illustrate the method as applied to producing a disk-shaped trilaminate microstructure such as shown at 134 in FIG. 1D. In this illustration, a trilaminate expanse 136, formed on layers 138, 140, 142, is formed on a sacrificial layer 144. The expanse is then irradiated with a focused excimer laser beam, such as indicated at 146, which is patterned (by upstream photomasking and imaging) to give a beam that is effective to photoablate the laminate in the areas corresponding to spaces between desired-size circular elements on the laminate, as indicated in FIG. 11B. This ablating is continued until the beam has cut through the entire laminate depth, as shown in FIG. 11C, forming the disc shaped microstructures on the sacrificial layer. Removal of the sacrificial layer gives the plurality of structures 134.

C. Microstructure Surface Structures

The term "molecular coating" is used herein to describe a coating which is bound to the surface (outer or interior) of a microstructure. The molecular coating may be bound directly to the surface of the device or bound to a lipid or a resin such as an electron donating group, e.g. —$NH_2$, OH or the like derivatized onto or associated with the surface of a structural layer of the device. The molecular coating may encompass all or a portion of the surface area of the device. Molecular coatings that can confer various characteristics or impart selected functional properties are described below.

Figure 12:
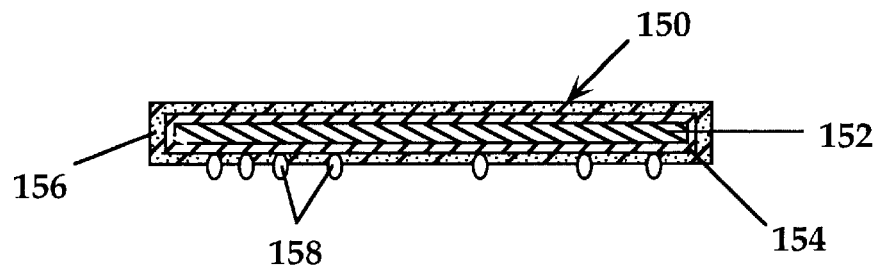
FIG. 12 is a sectional view of a coated microdevice.

FIG. 12 illustrates a general embodiment of a coated microdevice 150. A central layer 152 in the device is coated with a corrosion delay layer 154, such as gold or nickel, which is in turn coated with a layer of various molecules 156 that comprise the biochemical interface to the blood. The lower side of the device in the figure that will bind to the cell or tissue target (e.g., a capillary wall) is coated with ligand molecules 158, such as IgG antibodies, that are effective to specifically bind to the marker molecules on the target (e.g., tumor capillaries).

In one general embodiment, the molecular coating is a marker-binding agent, typically an antibody or antibody fragment, for targeting the microdevice to a specific cell type, e.g., tumor cell. A number of monoclonal antibodies to tumor-specific antigens are known to the art. See, for example, pp. 301–323 of CANCER, 3d Ed., De Vita, et al., Eds. Among the specific anti-tumor antibodies known are those that bind to pancarcinoma antigens (PCAs), an example of which is the tumor-associated glycoprotein antigen known as TAG-72. Such antibodies thus bind to a broad spectrum of cancers, and to different cellular mutations in the metastatic cascade. Examples of antibodies of this type are B-72.3 and the CC49 antibodies. Microdevices coated with anti-PCA antibodies are particularly useful in the diagnosis and treatment of different neoplasms.

To facilitate tracking of a therapeutic microdevice of the present invention, and/or to enable the use of diagnostic devices, one of the structural or coating elements of the microdevice may be designed to be detectable using, for example, X-radiation, scintigraphy, nuclear magnetic resonance, optical inspection (e.g., color, fluorescence), or ultrasound, as noted above.

A molecular coating may also be used to prevent or inhibit attachment of serum opsonins to the devices, to extend the blood circulation lifetime of the devices. As described below, such hydrophilic polymers may be conjugated to vesicle-forming lipids, and the microdevices can be coated with a lipid film containing such vesicle-forming lipids.

The microdevices may also be coated with a natural or synthetic glycocalyx to enhance its solubility. Other hydrophilic natural polymers, such as glycogen or polyserine, are also useful for this purpose, as are biocompatible detergents such as non-ionic polymerized oxyethylene ethers, e.g., "TRITON-X 100".

Figure 13A:
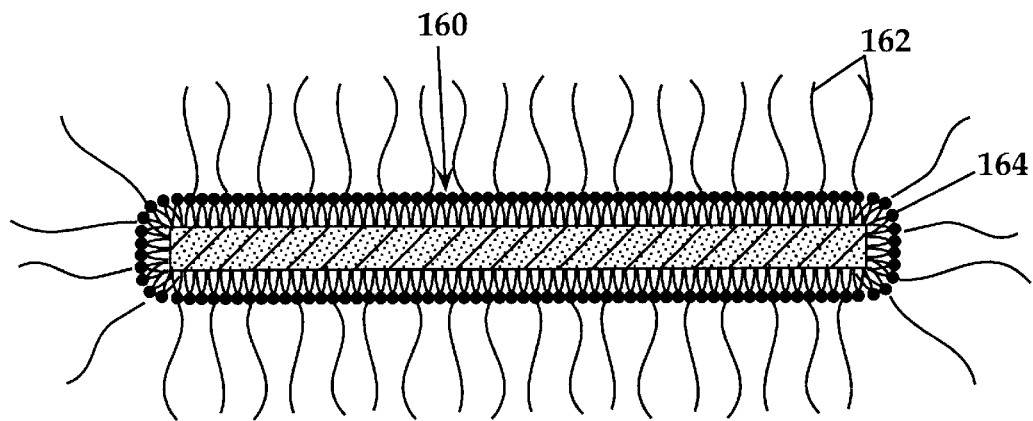
FIGS. 13A and 13B are sectional views of a lipid coated microdevice having a surface coating of hydrophilic polymers, where in FIG. 13B, a portion of the polymers have antibodies attached to their distal ends.

In one embodiment of a microdevice 160, shown in FIG. 13A, hydrophilic polymer chains, such as chains 162, are conjugated to vesicle-forming lipids (see for example, U.S. Pat. Nos. 5,013,556 and 5,213,804), which in turn are anchored in a lipid film 164 formed on the exterior surface of the microstructure. Methods for forming lipid films, such as lipid bilayer films, on particles are detailed for example, in above cited WO/US94/01924.

Examples of hydrophilic molecules suitable for conjugating to vesicle-forming lipids include polyethylene glycol chains having molecular weights between about 1,000 and 10,000 daltons. Other suitable hydrophilic molecules are polyvinylpyrrolidone (PVP), polymethyloxazoline, polyethyloxazoline, polyhydroxypropyl methacrylamide, polymethacrylamide and polydimethylacrylamide, polylactic acid, polyglycolic acid, and derivatized celluloses, such as hydroxymethylcellulose or hydroxyethylcellulose.

Figure 13B:
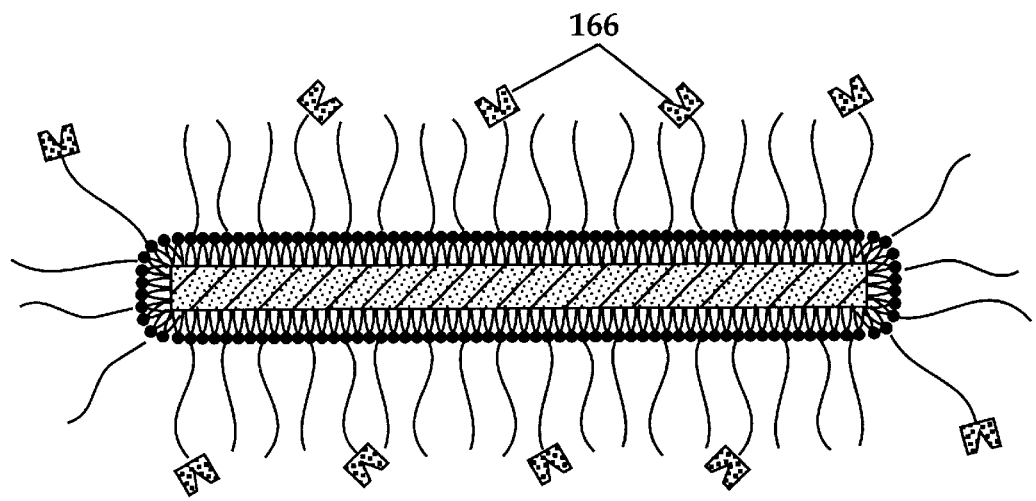

Referring to FIG. 13B, a portion of the hydrophilic polymer chains may additionally contain a marker-binding molecule 166 (i.e., a ligand) at their free end. Such marker-binding molecules may be conjugated to activated free ends of the hydrophilic molecules using known methods.

Figure 14:
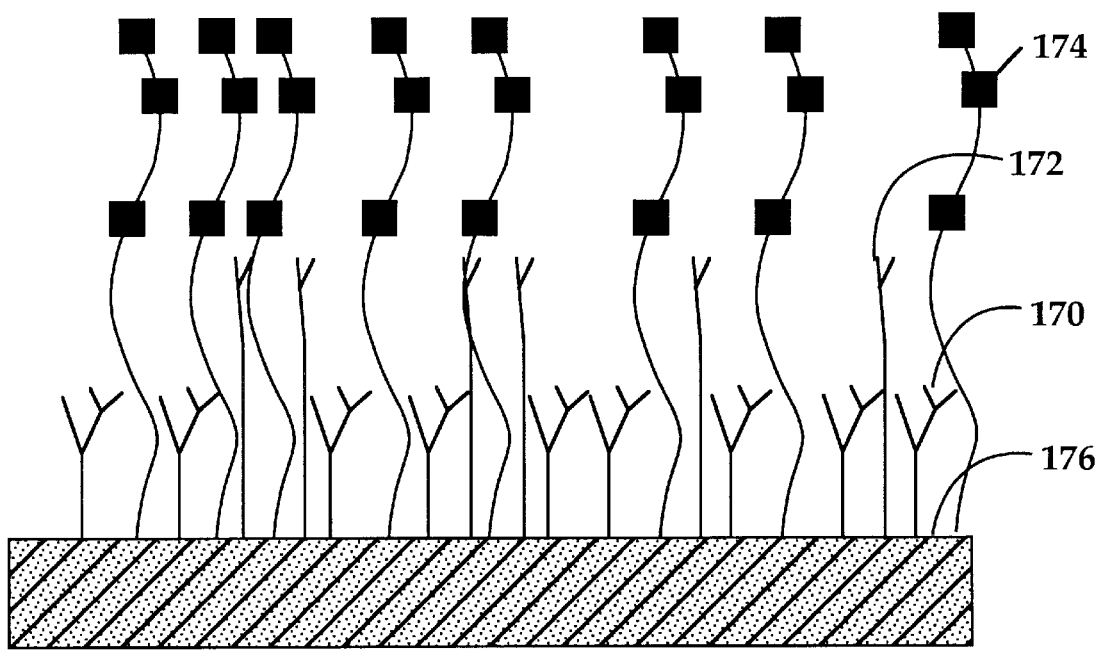
FIG. 14 is a sectional view of a microdevice having an upper surface coating of antibodies and a hydrophilic polymer.

FIG. 14 shows how a gradient of increasing hydrophobicity can be established by decreasing the number of hydrophobic groups, such as groups 170, 172, and increasing the number of hydrophilic groups, such as groups 174, per unit volume as a function of increasing distance from the surface of a device, here indicated at 176. A synthetic glycocalyx can thus be tailored to provide the functional coat desired for a particular device. A hydrophobic environment can be maintained near the surface of the device to harbor mobile hydrophobic groups, while the entire device is kept in suspension in an aqueous environment by hydrophilic groups on long chains.

D. Therapeutic Agents

Microdevices of the present invention consist of microfabricated structural elements (microstructures) in association with a therapeutic agent and any other functionality-enhancing agent or coating. The therapeutic agent may be (i) incorporated into the microdevice during microfabrication (either as a structural substrate or as a coating), or (ii) associated with the device after it is micromanufactured (e.g., by coating or conjugating it onto the device). As is described below, therapeutic agents such as drugs can be incorporated into matrices (e.g., polymer matrices) or otherwise formulated into therapeutic compositions which may be deposited into wells or pits manufactured into the devices.

Therapeutic agents associated with the microdevice after it is microfabricated include coatings of therapeutic biomolecules, such as therapeutic antibodies (e.g., antibodies directed against LDL or a viral antigen).

The activity of the therapeutic agent is expressed by exposure of the microdevice to the biochemical environment of the target site. The target site can be a particular location in the body, or the site of administration. For example, in the case where the target is a set of molecules circulating in the bloodstream, the biochemical environment of the target site is the blood. In cases where the target is a non-circulating tissue, such as a tumor, the biochemical environment of the target site is the environment in proximity to the tumor.

In another embodiment, the activity of the therapeutic agent is expressed by remotely activating the device with an external stimulus. This activation can be in place of or in addition to activation by exposure of the microdevice to the biochemical environment of the target site. In one example, the microdevice may be made to contain a therapeutic composition enclosed by wall or side portions which can be broken down or preferentially degraded by remote activation. For instance, the top and/or bottom surface of the device may be made of a material that is more brittle than the other portions of the device. Upon localization of the devices at the target site, mechanical (e.g., ultrasonic) stimulation may be applied to the target region, causing the brittle portion (cover) to rupture and release the drug. The activation may be made by ultrasound, such as in sonograms, with preferential frequency as close as possible to the resonant frequency of the cover plate.

To further enhance specificity of release and minimize "accidental" rupture of the cover described above, the cover material may be selected so that it is mechanically resistant and sufficiently deformable under regular physiological conditions, but becomes prone to dissolution or brittle fracture upon exposure to the biochemical environment at the target site. For example, the cover could be produced from a material that is relatively compliant at body temperature, but becomes more brittle at lower temperatures. Such microdevices may be employed, for example, in conjunction with localized cryotherapy of cancer and other pathologies.

Alternatively or in addition to the above, remote-activation properties may be imparted to devices of the invention by using cover materials which are rendered brittle or which simply dissolve in the presence of a chemical compound or composition injected at the target site. This is advantageous especially if the cover material is of organic nature, for example, made of collagen, a lipid bilayer, or 10–12 PDA. In these cases, suitable enzymes, such as matrix metalloproteinases, injected at the target site, may be used as the remote activation substance.

The cover may be fabricated at the same time as the shell, so that no bonding operations are required. However, microdevices that are obtained by bonding the cover to the shell following loading with the therapeutic agent are amenable to a different activation system, involving the degradation of the bonding material. This again may be triggered by localized temperature changes, or by the localized injection of degrading substances.

The therapeutic agent contained in the therapeutic devices of the present invention may be a releasable agent or an immobilized agent. A releasable agent is a therapeutic compound, such as a drug, that is designed to be released at a selected target in order to exert its therapeutic efficacy. An immobilized therapeutic agent is one that performs its therapeutic function while immobilized on the microdevice. For example, microdevices containing therapeutic antibodies as described above are an example of an immobilized therapeutic agent.

Microdevices of the present invention may be fashioned to deliver a selected therapeutic agent or ligand to a selected target in a form where the therapeutic agent is shielded from recognition by the subject's immune system. In one such embodiment, the therapeutic agent (e.g., an antibody directed against LDL or against a viral antigen) is attached to the bottom portion of a cup-shaped microdevice, as exemplified in FIG. 15. The microdevice shown, indicated at 180, has a tri-laminate structure consisting of two bottom layers 182, 184, and an upper layer 186, which defines an internal cavity 188. The exposed surface of layer 184, which forms the inside bottom of the cup-shaped microdevice, has a surface layer of covalently bound antibodies, such as antibodies 190. The material forming the device is selected for surface specific attachment of antibodies to the upper surface of layer 184. The exposed surfaces of layer 186 can be optionally coated with hydrophilic molecules, as indicated.

The diameter D of such a device is small enough (e.g., less than about 150 nm) and the thickness of layer 104 large enough (e.g., greater than about 30 nm) so that the cell membranes of an immune-response cell, such as indicated at 192, that may contact the device while it is in circulation cannot contact the layer of antibodies on the exposed surface of layer 184. By preventing such contact, the host immune response directed against therapeutic antibodies 190, while they are associated with the microdevice, will be decreased or eliminated.

E. Microdevice Suspension

The invention includes a suspension of microdevices of the type described above for use in administering a therapeutic agent to a selected target site in a subject. To form the suspension, microdevices as described above are suspended in an aqueous medium at a selected concentration. The optimal concentration will depend on the characteristics (e.g., solubilization properties) of the microdevice, type of therapeutic application and mode of administration. For example, compositions for oral administration can be relatively viscous, and may therefore contain a high concentration (e.g., >50%) of the microdevices. Solutions for bolus injections preferably contain a relatively concentrated suspension of microdevices (e.g., 10–50%), but not so concentrated that it has an appreciably higher viscosity than saline (to minimize need for large-bore needles). Solution used for continuous intravenous infusion typically contain a relatively low concentration (e.g., 2–10% suspension) of microdevices, due to the relatively large volumes of fluid that are administered.

The microdevices can be suspended in any suitable aqueous carrier vehicle. A suitable pharmaceutical carrier is one that is non-toxic to the recipient at the dosages and concentrations employed and is compatible with other ingredients in the formulation. Examples of suitable carrier vehicles include but are not limited to water, saline, Ringer's solution, dextrose solution, and 5% human serum albumin. Suspensions for use in injectable formulations are preferably isotonic with the subject's blood. Generally, the carrier can contain minor amounts of additives such as substances that enhance isotonicity and chemical stability, e.g., buffers and preservatives, as well as low molecular weight (less than about 10 residues) polypeptides, proteins, amino acids, carbohydrates including glucose or dextrans, chelating agents such as EDTA, or other excipients.

Prior to administration to a subject, the suspension of microdevices is sterilized by a suitable sterilization method. Heat-stable microdevices can be heat-sterilized, e.g., using an autoclave. Microdevices that are not heat-stable may be sterilized by passage through a commercially-available sterilization filter, e.g., a 0.2 $\mu$m filter. Of course, filtration may be used only in cases where the microdevice is smaller than the pores of the sterilizing filter.

III. Applications

Microdevices of the present invention can be administered to a subject in need of therapeutic intervention via any suitable administration method. The particular method employed for a specific application is determined by the attending physician. Typically, the microdevices will be administered by one of the following routes: topical, parenteral, inhalation, oral, vaginal and anal.

As discussed above, microdevices of the present invention are particularly useful in treatment of malignant tumors. In these applications, the type of tumor influences the mode of administration. For example, skin cancer may be treated by topical application of, preferably, a viscous suspension; lung cancer may be treated by inhalation of an aerosolized aqueous microdevice suspension; cervical cancer may be treated by vaginal administration of a microdevice suspension; and colon cancer may be treated by rectal administration of such a suspension.

The majority of therapeutic applications involve some type of parenteral administration, which includes intravenous (i.v.), intramuscular (i.m.) and subcutaneous (s.c.) injection. Microdevices suitable for parenteral administration preferably have a selected maximum dimension in the range between 0.1 and 3 microns. Specific examples of devices useful for parenteral administration, particularly intravascular administration, are described below.

Administration of the microdevices can be systemic or local. The non-parenteral examples of administration recited above, as well as i.m. and s.c. injections, are examples of local administration. Intravascular administration can be either local or systemic. Local intravascular delivery can be used to bring a therapeutic substance to the vicinity of a known lesion by use of guided catheter system, such as a CAT-scan guided catheter. General injection, such as a bolus i.v. injection or continuous/trickle-feed i.v. infusion are typically systemic.

In a preferred embodiment, the microdevices of the present invention are injected into the blood stream and allowed to circulate and localize to their target. Exemplary targets include different types of freely-circulating molecules, cells and/or tissues accessible via the circulatory system. The effectiveness of the microdevices in these applications is potentially affected by several factors, including the subject's immune response directed against the microdevices, and the solubility of the devices in circulation. Both factors can be addressed by coating the microdevices with appropriate coatings, such as polymer coatings, as discussed above.

A. Targeting Circulating Molecules and Viruses

Figure 15:
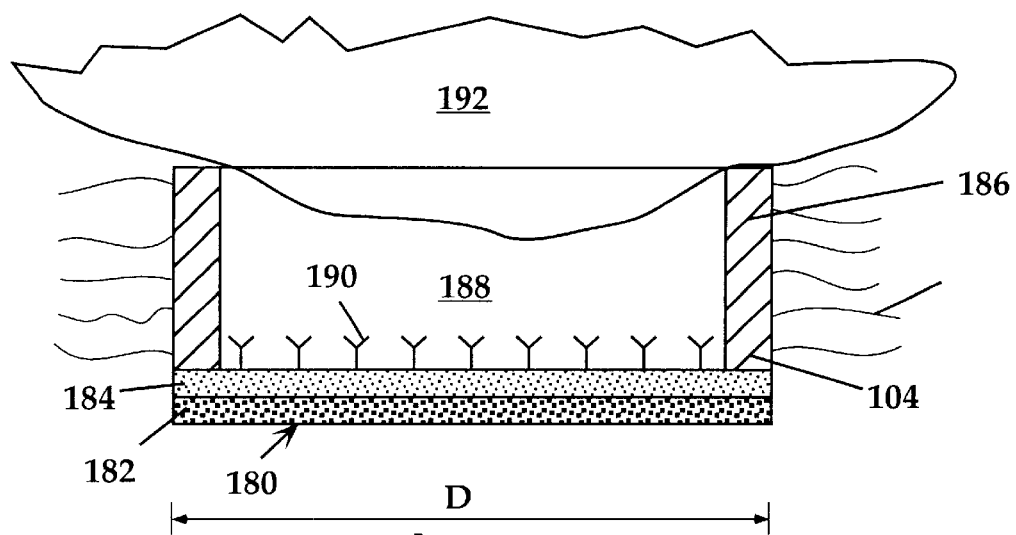
FIG. 15 is a sectional view of a microdevice of the type shown in FIG. 6A, illustrating how the device structure shields antibodies carried on the device from contact with an immune-response cell.

In one general application of the present invention, the microdevices described herein are derivatized to contain an antibody or ligand effective to bind to a circulating blood molecule, and are used therapeutically to reduce the concentration of the circulating blood molecule. The microdevice used for such an application preferably contains the antibody or ligand in a manner that protects the antibody or ligand from attack by the subject's immune system. An example of such a configuration is shown in FIG. 15.

By way of example, such microdevices may be derivatized to contain antibodies directed against very low density lipoproteins (VLDLs) and/or low density lipoproteins (LDLs), elevated levels of which are associated with increased risk of coronary heart disease in humans. The therapeutic agents in such microdevices are the anti-LDL and anti-VLDL antibodies. The activity of the therapeutic agents (i.e., antibodies) is expressed by exposure of the microdevice to the biochemical environment of the target site, i.e., upon injection into the bloodstream. The expression of therapeutic activity is manifested in this example by the antibodies' binding of VLDLs and LDLs in the bloodstream. Such antibody-containing microdevices are preferably microfabricated using structural compositions that biodegrade after a selected period of time, e.g., several hours to several days. Once the structural portions of the microdevices have degraded, the LDL-antibody and/or VLDL-antibody complexes are released and degraded by macrophages.

B. Targeting Cells and/or Tissues

Microdevices of the present invention may be used to target and deliver therapeutic compound(s) to selected cellular or tissue targets. The cells may be circulating cells, such as mononucleated blood cells (MBCs), bacterial cells in a systemic infection, etc., or non-circulating cells, such as cells comprising a fixed tumor mass, or the epithelial cells forming the lining of vessel or capillaries. Any cell-specific molecular marker may be detected by the methods of the invention so long as the device is fabricated with a marker-specific ligand or antibody. In a preferred embodiment, the molecular markers to be identified are tumor-specific antigens. In selecting specific antibodies for in vivo applications, an efficient strategy is to use human antibodies specific for the common generic molecules that are relatively more plentiful in target diseased tissue cell membranes than in healthy cell membranes.

Figure 16A:
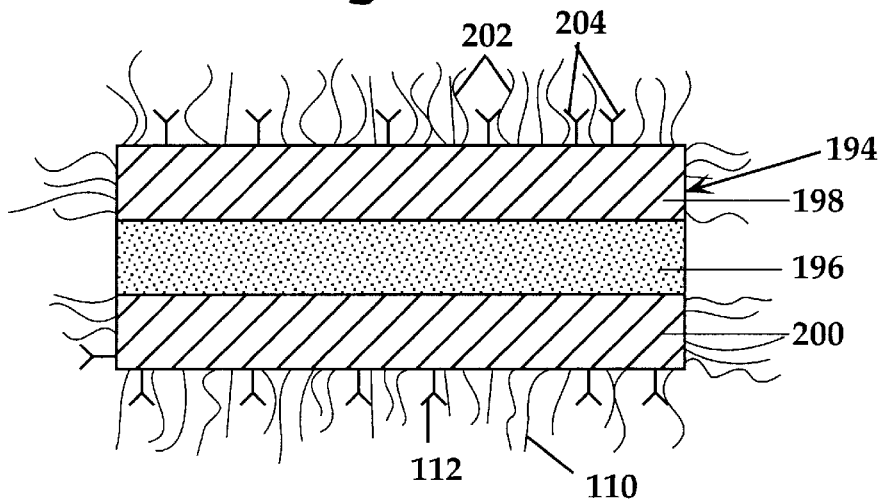
FIGS. 16A and 16B are sectional views of a microdevice of the type illustrated in FIG. 3A, showing more rapid erosion of a middle drug-carrying layer in the microdevice.
Figure 16B:
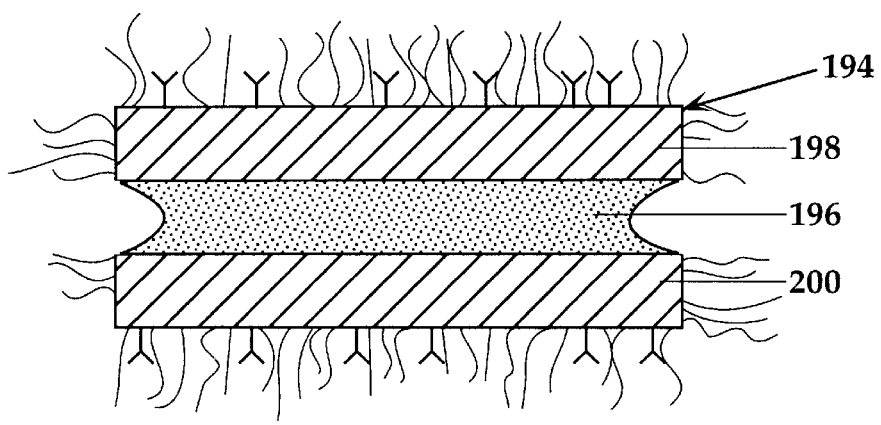

An exemplary microdevice 194 useful for targeting a tissue in need of exposure to a therapeutic agent is shown in FIGS. 16A and 16B. The device has a trilaminate structure consisting of a therapeutic-agent-containing layer 196 sandwiched between two targeting/support layers 198, 200. The exposed surfaces of the support layers can be coated with, e.g., (i) hydrophilic molecules, such as molecules 202, to improve the suspension or circulation characteristics of the device, and (ii) binding molecules, such as antibody molecules 204, directed against a marker on the target cell or tissue.

In one embodiment, the therapeutic-containing layer erodes at a faster rate than the outer, targeting/support layers. This feature, illustrated by the partially-eroded middle layer in FIG. 16B, allows the microdevice to remain securely attached to the target even as the therapeutic layer dissolves away. A related embodiment has a bilaminar structure consisting of one therapeutic layer and one targeting/support layer as described above, where the therapeutic layer dissolves at a faster rate than the targeting/support layer.

When targeting noncirculating cells inside capillaries (e.g., the endothelial lining), the binding between the device and the molecular marker should be sufficiently strong to overcome the drag force exerted by the flowing blood. This objective can be satisfied by having a relatively large, planar surface area for specific binding and a relatively low profile in the capillary's blood-flow space.

Figure 17A:
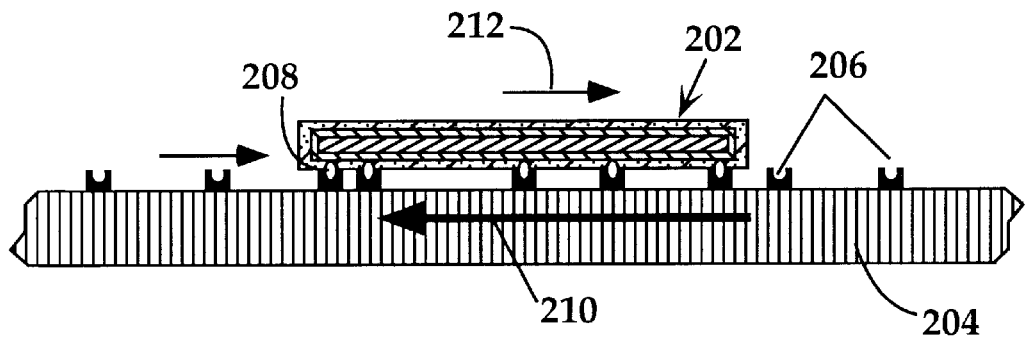
FIGS. 17A and 17B illustrate the greater surface contact between a drug-delivery particle or capillary wall surface in a disc shaped particle constructed in accordance with the invention (17A) than in a conventional self-assembly type spherical drug-delivery particle (17B)

Referring to FIG. 17A, a disk-shaped microdevice 202 is attached to capillary wall 204 via interactions between marker molecules 206 on the capillary wall and ligand molecules 208 on the device's surface. Epithelial cell markers which are specific for certain pathologies, e.g., tumors, have been identified.

It will be appreciated that a microdevice having a configuration as illustrated in FIG. 17A is able to effectively utilize the binding interactions between the microdevice and the capillary wall to resist the forces due to blood flow (represented by arrows 212) which act to displace and move the device in a downstream direction. As illustrated, the shear force 210 due to these binding interactions is greater than the sum of the blood flow forces 212.

Figure 17B:
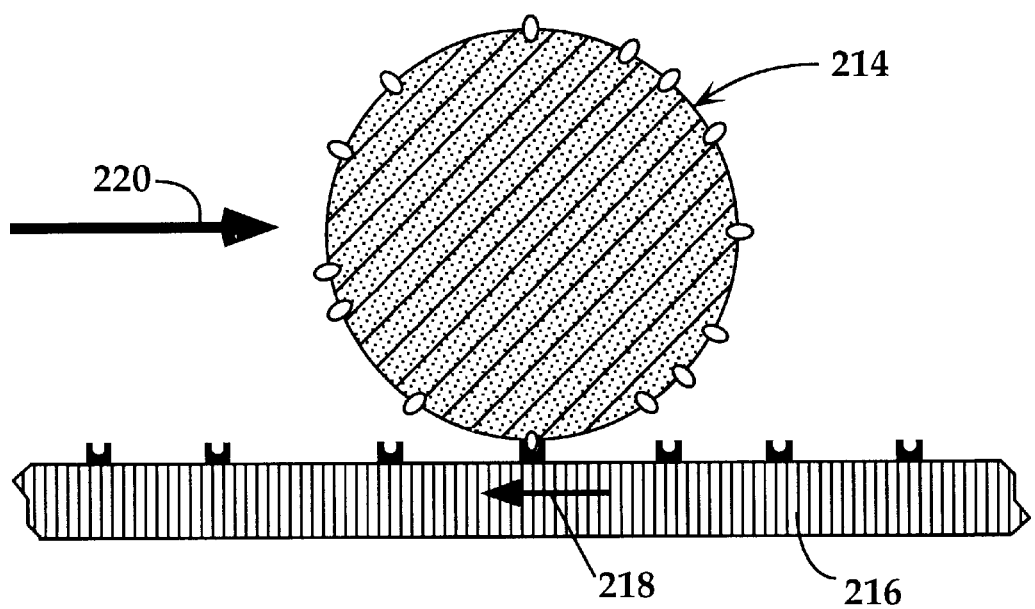

By comparison, FIG. 17B shows a cross section of a spherical microparticle 214 bound by ligand-specific interactions on a capillary wall 216. Here the ratio of area of device contact with the capillary wall to the device's profile in the region of blood flow is quite low, as can be appreciated from the Figure. Accordingly the shear force holding the particle to the capillary wall, indicated by arrow 218, is smaller than the force due to blood flow, indicated by arrow 220, giving an unstable binding condition.

The same factors, particularly the high surface area of contact, produces enhanced binding between microdevices of the invention having substantially planar surfaces, and cell surfaces.

C. Transluminal Targeting

The invention further provides a therapeutic method in which a microdevice crosses the vascular membrane to a preselected site for delivery of a therapeutic agent. In one embodiment, the microdevice is coated with a ligand to the endothelial or basement membrane of a neoplastic cell. Examples of ligands targeting the basement membrane are an anti-collagen type I, IV, V, anti-fibronectin, anti-proteoglycans and anti-laminin antibodies. In a preferred embodiment, the ligand is anti-collagen IV antibody. The device is designed so that, upon binding to the target cell, it migrates into the underlying tissue and delivers the therapeutic agent.

Figure 18A:
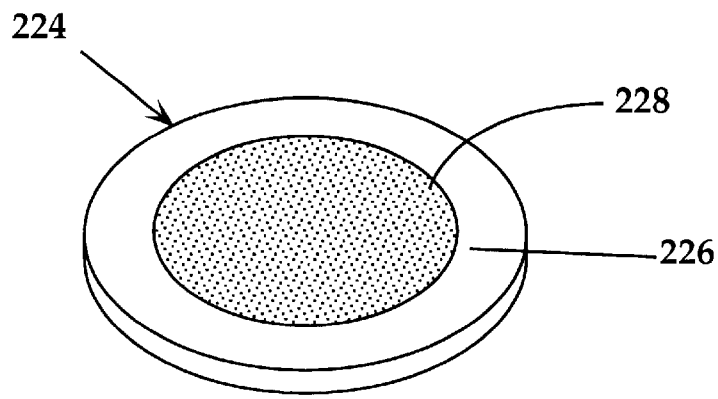
FIGS. 18A–18C are embodiments of the invention suitable for treatment of interstitial tissue.
Figure 18B:
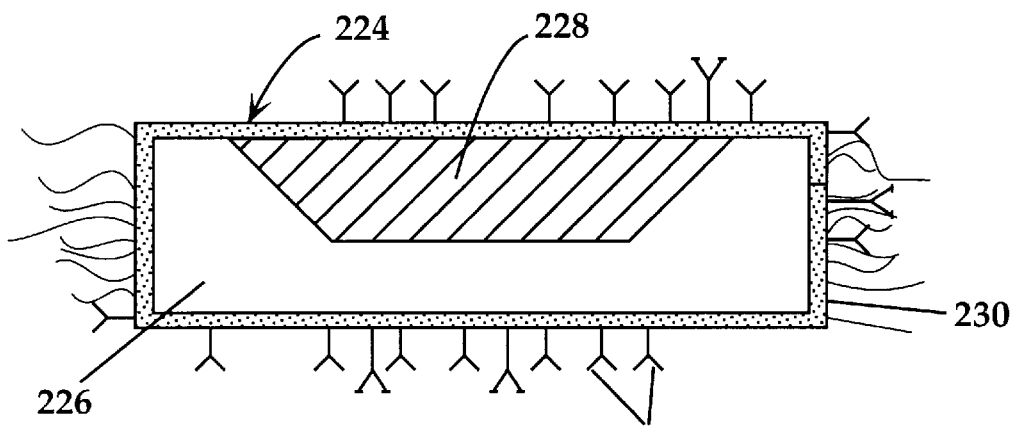

For the illustration of these uses, reference is made to a microdevice 224 in FIG. 18A, composed of a microstructure 226 and a core 228. A cross-sectional view of the device is given in FIG. 18B. The device may be protected with an anticorrosion layer, such as layer 230, which may be selected to have different thicknesses in its microstructure and core surface areas. Also as shown, the outer surface may be coated with hydrophilic polymers, such as described above, and antibody molecules, such as molecules 232, for capillary-wall targeting.

Figure 18C:
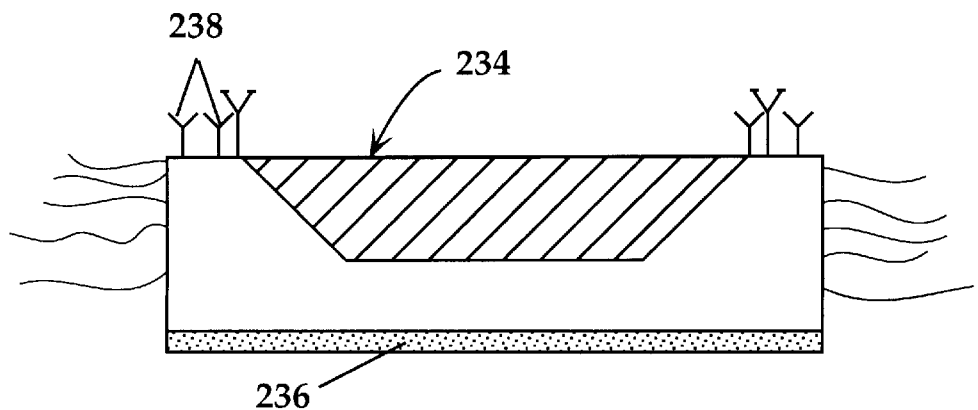

Another embodiment of the microdevice, indicated generally at 234, is shown in FIG. 18C, with an anti-corrosion coating 236 present only on the inferior surface, hydrophilic polymer chains only on the lateral surface, and targeting antibodies, such as at 238, only on upper portions of the device, as shown.

Figure 19A:
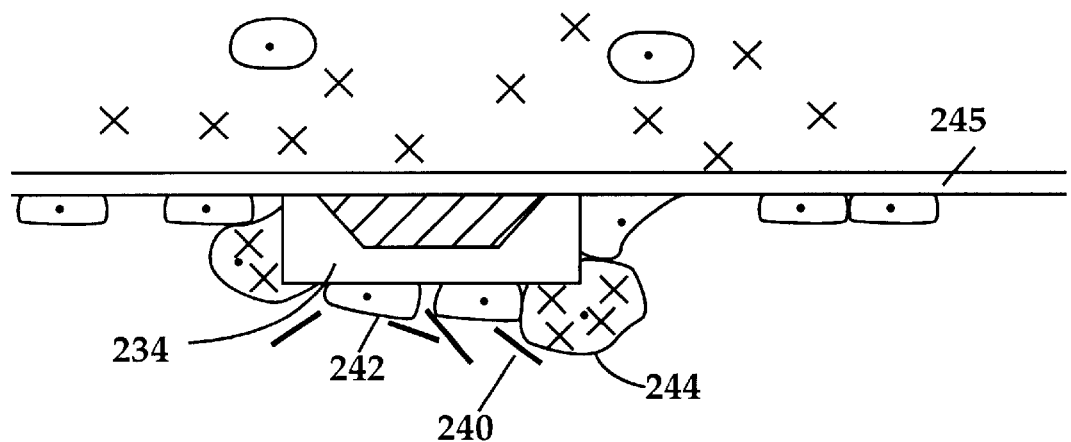
FIGS. 19A and 19B illustrates steps in the movement of a microdevice constructed in accordance with one embodiment of the invention across an epithelial membrane.
Figure 19B:
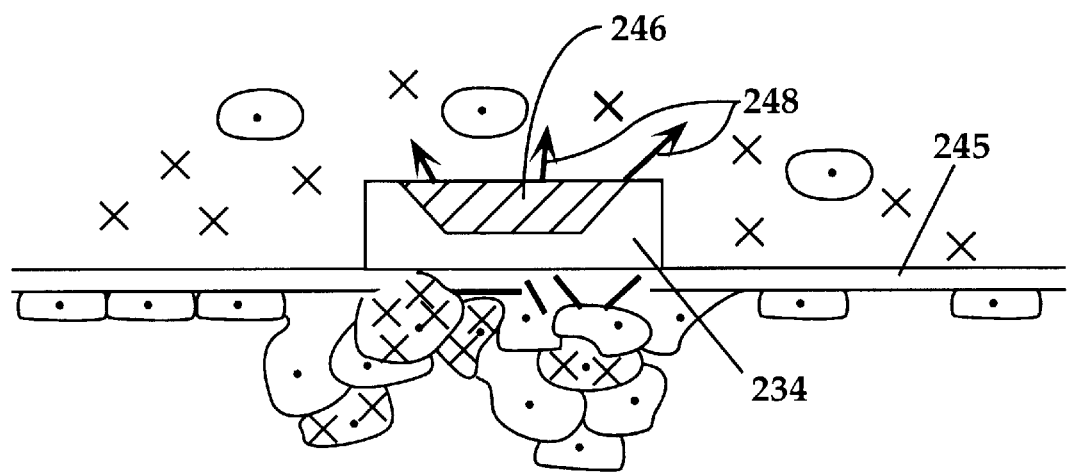

FIGS. 19A and 19B illustrate the method by which the microdevices are able to cross a vascular-wall membrane or wall, such as indicated at 245. The illustration is with respect to microdevice 234 shown in FIG. 18A, and containing anti-collagen IV antibodies on its upper surface in that figure. After i.v. administration, and migration to the target capillary wall surface, the anti-collagen IV antibodies adhere to the subendothelial basement membrane (FIG. 19A). The endothelial cells tend to retract when contacted from their luminal surface, and subsequently to migrate over bodies contacting the continuous basement membrane, so as to separate such bodies from the circulation. These processes underlie well-known biological actions such as the repair of cuts in the vessels walls, and the extravasation of tumor cells from both venules and arterioles to initiate metastatic cascades. The time required for the reaching of a configuration such as shown in FIG. 19A is about 2–4 hours. The microdevice may be coated with an anti-corrosion layer designed to allow for such a time interval, with an appropriate safety factor. The microdevice may be complexed on its passive (open) side by fibrin 240, platelets 242, and immune cells 244, as shown.

Different functions may be assigned to the device's core, indicated at 246. The first of these is lysis or dissolution of the basement membrane. For this purpose, the core may consist exclusively or partially of substances or biological entities that degrade such membranes. Examples are matrix-degrading enzymes among serine proteinases, neutral metalloproteinases, and cysteine proteinases. In a preferred embodiment, microdevice core contains type IV collagenase, a metalloproteinase that is specific to collagen type IV, and thus particularly efficient for the lysis of the basement membrane.

After binding of the microdevice to the walls of the target vasculature, the membrane-degrading agent within the core is released, and gradually dissolves the basement membrane. The device thus penetrates the cell stroma, while membrane reconstruction takes place by natural processes. A configuration such as shown in FIG. 19B is reached, with the microdevice stably lodged within the interstitium. The extravasation process requires about 2–12 hours.

At any time following binding, membrane lysis, and/or transluminal migration, other functions may be performed, including the delivery from the microdevice of therapeutic agents appropriate to the pathology being treated. The diffusion of such therapeutic agents to the targeted tissue is indicated by arrows 248 in FIG. 19B. For the treatment of neoplasms, preferred therapeutic agents include anti-cancer drugs, including antimetabolites, alkylating agents, plant alkaloids, and antitumor antibiotics; biological agents, including monoclonal antibodies, interferons, and interleukins; chemosensitizers, i.e., chemicals that decrease the resistance of cells to drugs, such as misonidazol and its analogs; and radiosensitizers, or compounds which enhance the sensitivity of tumor cells to radiation, e.g., halogenated pyrimidines, and compounds that radiosensitize hypoxic cells, e.g., nitroimadizole compounds.

D. Tumor Targeting

In one embodiment, microdevices are designed for the in vivo treatment or detection of tumors by extravasation. This targeting occurs by circulation of the microparticles through the bloodstream, over an extended time period, and passive extravasation of the devices through compromised regions of the vasculature, which tend to correspond to vascular regions servicing a solid tumor. The microdevices therefore have a preferred maximum dimension of less than about 150–200 nm, to allow for passive transit through the compromised vasculature, and a hydrophilic surface coating to ensure prolonged blood circulation lifetime.

In one embodiment, tumor-targeted microdevices are produced for use with boron neutron capture therapy (BNCT). BNCT is a method of delivering high energy radiation to kill selected tissues, typically tumors, and employs two separately nonlethal components—a radiosensitizing compound that contains a stable boron-10($^{10}$B) isotope, and nonionizing neutron radiation. The boron-10($^{10}$B) isotope is administered in the form of a suitable boronated agent, which is targeted to tumor cells, e.g., using microdevices of the invention. At an appropriate time after the boron-containing devices are administered, the tumor cells are exposed to thermal neutrons (typically produced by a small nuclear reactor). The thermal neutrons interact with the boron-10 in a nuclear reaction that yields helium nuclei ($\alpha$-particle) and lithium nuclei having about 100 million times more energy than the initial neutron irradiation. The energy from these highly-energetic charged particles, however, is dissipated within a few cell diameters, minimizing damage to tissue that either does not contain the boron compound, or that is not irradiated. Accordingly, selectivity is achieved through the use of boron-containing microdevices selectively targeted to tumor cells as described above, and/or by aiming the neutron beam at the targeted tumor mass.

Many classes of compounds have been synthesized for use with BNCT (see, e.g., Barth, et al., *Cancer* 70:2995–3008 (1992); Fairchild, et al., *Cancer Res.* 50:4860–4865 (1990); and Zamenhof, et al., *J. Nat'l. Cancer Inst.* 84:1290–1291 (1992). Examples of boron-containing compounds include $Na_2B_{12}H_{11}SH$ (sodium borocaptate or BSH), p-boronophenylalanine (BPA), p-carboxybenzeneboronic acid, sodium decahydrodecaborate, $B_{12}H_{11}SH^{2-}$, $B_{10}Cl_9(SH)_2^{2-}$, boronated amino and polyamino acids, including boronated polylysine; [N-succinimidyl-3-(undecahydrododecaboranyldithio)propionate, and carborane-containing amino acids, carborane-containing promazine, carborane-containing porphyrins, and other polyhedral boranes. See, for example, Barth, et al., *Cancer,* 70:2995–3008 (1992), and Hawthorne, *Angew. Chem. Int. Ed. Engl.* 32:950–984 (1993). Such boron-containing compounds may be incorporated into the microdevices of the invention either during or after microfabrication, as described above.

The boron-containing microdevices are then administered to the patient as described herein, allowed to localize, and the treatment volume is exposed to a field of thermal neutrons from a small nuclear reactor or a particle accelerator-based system, as is known in the art. For example, in Japan, the neutron beams used for BNCT have a characteristic neutron energy that corresponds at incidence to thermal equilibrium with tissue at body temperature (about 0.025 eV). In the US and Europe, epithermal-neutron beams (energies in the range of 1 eV to 10 KeV) have been used because they penetrate deeper into the irradiation volume before slowing to thermal energy, yet they are still not of sufficient energy to inflict unacceptable damage to intervening normal tissues.

E. Targeting by External Magnetic Field

Figure 20:
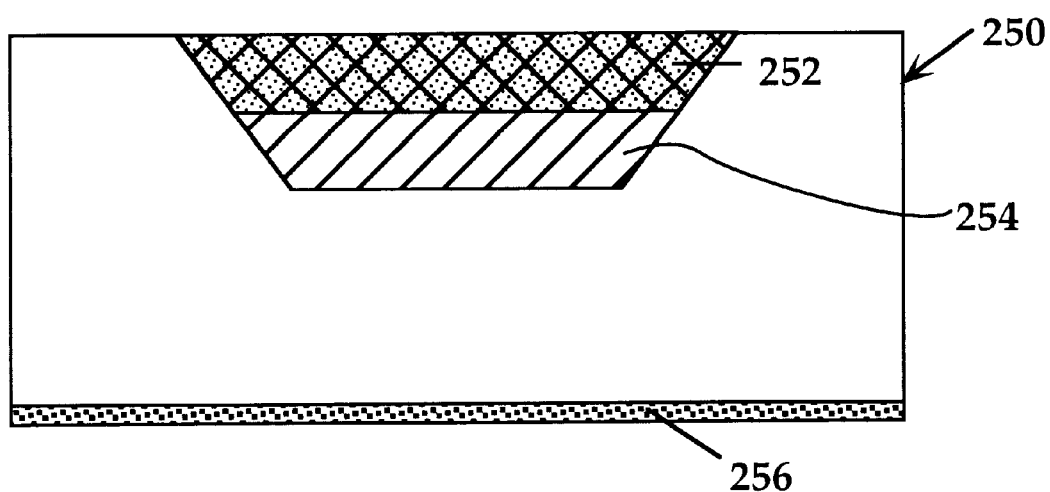
FIG. 20 is a cross section view of a microdevice containing a magnetic layer.

In another embodiment of the invention, the microdevices are fabricated to include a strong magnetic subdomain. An example is illustrated in FIG. 20 showing a microdevice 250 having a core which in this case contains two different core layers, such as layers 252, 254, and a magnetic layer 256 by which the particles can be guided in the body by an external magnetic field. In one application, unattached magnetic devices can be removed from the circulation of a subject by, for example, providing a segment of extracorporeal circulation, and removing the free floating devices by magnetic action in the extracorporeal segment. Magnetic removal of particles from biological fluids for in vitro applications is taught in U.S. Pat. Nos. 4,018,886 and 3,970,518.

When appropriate, the devices may be limited to circulate within localized diseased areas by application of localized magnetic fields. For example, a device containing a magnetic core as well as appropriate therapeutic agent(s) is administered locally or systemically, and a local magnetic field applied to the diseased region. This is a useful procedure for the treatment of some lesions for cases in which surgical excision is not desirable, or possible. Such cases include melanoma with multiple superficial metastases and penile cancer. The concentration of radioactive tags with magnetic particles in vitro is taught in U.S. Pat. No. 3,993, 997.

For chemotherapeutic therapies, localized magnetic fields can be used as described above for concentrating radiotherapeutic microdevices in known diseased sites. This is a useful procedure for the treatment of superficial lesions for cases in which surgical excision is not desirable, or possible.

Magnetic devices may also be useful in monitoring the targeting of the devices using magnetic resonance imaging (MRI).

F. Targeting Intraoperatively

The device of the invention may be used for intra-operative diagnosis and intra-operative treatment of metastatic domains. For this application, the device carries antibodies to target antigens expressed on the surface of neoplastic tissue. Examples of such antibodies include anti-collagen IV antibodies, for the cases of breast and colon cancers, as well as lymph node metastases of the former. The device core can contain any desired combination of therapeutic agents, such as antimetabolites, alkylating agents, plant alkaloids, antitumor antibiotics, monoclonal antibodies, interferons, interleukins, chemo-sensitizers, and the like. In the course of surgery directed to the removal of an identified large lesion, a suspension of microdevices in physiological fluid is applied to a region adjacent or related to the main lesion, if such area is suspected of metastatic infiltration. The microdevices that do not bind to the tumor antigens in the area of exposure are removed, e.g., by washing, suction, or magnetically, as described above. The bound devices identify the existence of metastatic domains, which the surgeon may elect to remove. However, even if these are not removed, therapeutic action against them is provided by the therapeutic agents loaded within the microdevices. The limits or eliminates the necessity for follow-up or adjuvant chemotherapeutic or radiotherapeutic treatment of metastatic colonies.

It will be appreciated from the foregoing that the present invention provides a number of advantages in therapeutic delivery composition over prior art particle compositions.

The microdevice particles employed can be designed with selected shapes, preferably having at least one planar surface, for enhanced ligand-specific binding to target cells. Further the particle sizes and shapes are effectively uniform, and can be made as small as existing types of "nanoparticles".

The devices can be designed with a number of discrete functions, include surface binding, suspension and RES-evasion functions, and one or more different therapeutic agents contained in separate compartments for different release rates.

The particles may be constructed of a variety of different materials, to achieve optimal and differential drug release at a target site. One of these materials may be a radiopaque material, such as a metal for visualizing the biodistribution of the particles, or a ferromagnetic material to allow magnetic field particle guidance.

In one embodiment, the microdevice has a core in which foreign therapeutic agents, such as antibodies and/or enzymes can be shielded from the host's immune system, allowing a variety of novel applications for clearing undesired serum components.

In still another embodiment, the microparticles are designed for either passive extravasation into solid tumors, or active transluminal movement through a combination of capillary-specific binding and partial membrane degradation.

Although the invention has been described with respect to specific embodiments and applications, it will be appreciated that a variety of changes and modifications may be made without departing from the invention as claimed.

What is claimed is:

1. A suspension of microdevices for use in delivering a therapeutic compound to the interstitial space of a target region which is characterized by a target-specific marker on a basement membrane forming a vasculature of the target region, comprising a suspension of microdevices in an aqueous medium, said microdevices (i) having a selected non-spherical shape, uniform dimensions and a selected maximum dimension in a range of 0.1 and 3 microns and (ii) composed of at least two separate bodies, including a support having at least one planar surface, and a therapeutic agent attached to the support, said therapeutic agent being in a form such that the activity of the therapeutic agent is expressed in direct response to a chemical or biochemical interaction that occurs upon exposure of the microdevice to a biochemical environment of a target site after administration of the microdevices to a subject, said microdevices containing a surface-bound marker-binding molecule effective to bind to such marker, and an enzyme effective to lyse the basement membrane.

2. The suspension of claim 1, wherein said enzyme is a type IV collagenase.

3. The suspension of claim 1, wherein said enzyme is covalently attached to a surface region of the microdevices.

4. The suspension of claim 1, wherein said enzyme is contained in said microdevices in releasable form, and the enzyme is released from said microdevices upon microdevice bioerosion.

5. A suspension of microdevices for use in administering a therapeutic agent to a selected target site in a subject, comprising a suspension of microdevices in an aqueous medium, said microdevices (i) having a selected non-spherical shape and uniform dimensions and (ii) composed of at least two separate bodies, including a support having at least one planar surface, and a therapeutic agent attached to the support, said therapeutic agent being in a form such that an activity of the therapeutic agent is expressed in direct response to a chemical or biochemical interaction that occurs upon exposure of the microdevice to a biochemical environment of the target site after administration of the microdevices to the subject, wherein the microdevices are substantially disc-shaped, and have a laminated structure containing first and second disc-shaped layers forming said support and therapeutic agent, respectively.

6. The suspension of claim 5, wherein the microdevices have a trilaminate structure composed of an interior layer forming said therapeutic agent sandwiched between a pair of exterior coating layers at least one of which forms said support, and the coating layers have a slower rate of bioerosion than the interior layer.

7. A suspension of microdevices for use in administering a therapeutic agent to a selected target site in a subject, comprising a suspension of microdevices in an aqueous medium, said microdevices (i) having a selected non-spherical shape and uniform dimensions and (ii) composed of at least two separate bodies, including a support having at least one planar surface, and a therapeutic agent attached to the support, said therapeutic agent being in a form such that an activity of the therapeutic agent is expressed in direct response to a chemical or biochemical interaction that occurs upon exposure of the microdevice to a biochemical environment of the target site after administration of the microdevices to the subject, wherein the microdevices have substantially disk-shaped supports having radially-disposed regions which contain said therapeutic agent.

* * * * *